United States Patent [19]

Kelman

[11] Patent Number: 4,678,469
[45] Date of Patent: Jul. 7, 1987

[54] INTRAOCULAR LENS WITH LARE-INHIBITING CLOSURE, THE METHOD OF INHIBITING GLARE, AND THE CLOSURE FOR SAME

[76] Inventor: Charles D. Kelman, 269 Grand Central Parkway, Floral Park, N.Y. 11005

[21] Appl. No.: 921,222

[22] Filed: Oct. 20, 1986

[51] Int. Cl.$^4$ ............................................. A61F 2/16
[52] U.S. Cl. ............................................. 623/6
[58] Field of Search ............................................. 623/6

[56] References Cited

U.S. PATENT DOCUMENTS 4,578,078 3/1986 Arkell ................................. 623/6
4,596,578 6/1986 Kelman ................................. 623/6

*Primary Examiner*—Richard J. Apley
*Assistant Examiner*—James Prizant
*Attorney, Agent, or Firm*—Henry Sternberg

[57] ABSTRACT

An intraocular lens having an optic with a positioning hole therein in the form of a through-bore adapted to selectively receive therein either the working tip of a surgical instrument used to manipulate the lens for seating in the eye or a plug for closing the bore. The plug is colored, frosted, or otherwise formed to be at least partially opaque to the passage of light therethrough to thereby substantially reduce the glare-effect which would otherwise be perceived by the user. Means are provided for releasably retaining the plug in the bore.

The method of inhibiting the passage of light rays through a positioning hole in an intraocular lens, after the lens is seated in the eye, to substantially reduce the glare-effect.

19 Claims, 11 Drawing Figures

# INTRAOCULAR LENS WITH GLARE-INHIBITING CLOSURE, THE METHOD OF INHIBITING GLARE, AND THE CLOSURE FOR SAME

FIELD OF THE INVENTION

This invention relates to intraocular lenses for the human eye, and, more particularly, to intraocular lenses of the type which have a positioning hole and which can be positioned in the anterior chamber, the posterior chamber, or partially in the anterior chamber and partially in the posterior chamber of the eye.

BACKGROUND OF THE INVENTION

Conventionally, in the seating of intraocular lenses, such as, for example, the lenses described and claimed in my U.S. Pat. No. 4,253,200 issued Mar. 3, 1981, such a lens is inserted into the eye through a corneo-scleral incision that may be also used to remove a natural lens. For seating such an intraocular lens in the eye it is typically provided with one or more openings, usually in the form of one or more bores, or positioning holes, allowing the surgeon to manipulate the lens into seating position by use of a surgical instrument whose tip is inserted into such positioning hole. The positioning holes, however, are conventionally located in the optic proper and have the disadvantage that, even though they are typically located near the periphery of the optic, they frequently result in the patient perceiving a glare-effect, particularly if the lens becomes decentered after implantation and such positioning hole is displaced toward the optical axis. It must be remembered, in this connection, that the peripheral wall of such positioning hole forms a boundary between the material of the optic, usually polymethylmethacrylate (PMMA) and the fluid within the eye which fills the hole when the lens is seated in the eye. A boundary between materials having such vastly different indices of refraction as the PMMA of the lens body, on the one hand, and the agueous humor in the eye, on the other hand, can cause a glare effect perceived by the user.

OBJECTS OF THE INVENTION

It is an object of the present invention, therefore, to provide a new and improved intraocular lens which avoids one or more of the disadvantages of prior such lenses.

It is another object of the invention to provide a new and improved intraocular lens which is constructed so as to minimize the glare which would otherwise result during use.

It is still another object of the invention to provide a new and improved intraocular lens, which inhibits undesirable glare from positioning holes even when the lens is decentered.

It is yet another object of the invention to provide a glare-inhibiting closure for the positioning hole of intraocular lenses.

It is a further object of this invention to provide a method for inhibiting the glare effect caused by the positioning hole of an intraocular lens.

It is a concomitant object of the invention to provide a new and improved intraocular lens which has an instrument-receiving positioning hole and glare inhibiting means associated with that hole.

Glare effect is produced whenever there is located, in the path of the light rays which pass through the pupil to the retina, an edge or similar boundary between regions which are both substantially transparent as distinguished from one of them being substantially opaque or at least not substantially transparent. For example, glare effect is likely to result if a lens is decentered and light rays passing through the pupil pass through the positioning hole, specifically, through the optically transparent fluid of the eye, exhibiting a given index of refraction, which fills such hole, while adjacent rays pass through the optically transparent material of the optic itself, exhibiting a different index of refraction. Such glare may be eliminated or at least minimized, however, by masking the positioning hole after the lens has been seated in the eye, providing an effect similar to that provided by the human iris. It is well known that due to its opacity the iris "masks" without any resulting glare-effect.

SUMMARY OF THE INVENTION

In accordance with the invention, an intraocular lens comprises a lens body, or optic, for focusing light rays on the retina of an eye. The lens body has an instrument-receiving positioning hole, or bore and masking means insertable into and removable from such bore, after the lens is seated in the eye, for masking the edge regions of the bore to eliminate or inhibit the glare effect otherwise resulting from light rays passing thru such bore. The masking means prevents, light rays which are directed toward the edge regions of such bore from passing therethrough in a recognizable, i.e. undiffused, form toward the retina, after the lens has been seated in an eye.

According to a preferred embodiment of the invention there is provided a lens body comprising anterior and posterior optically polished surfaces shaped to focus, on the retina, light rays entering the eye. A positioning hole in the form of a bore is provided in the lens body extending from one toward the other of said surfaces. The bore is adapted to receive therein the tip of a surgical instrument used to manipulate the lens body within the eye. Plug means, incorporating masking means are provided and are adapted to cooperate with the bore for preventing light rays in the region of the periphery of the bore from continuing toward the retina in a recognizable, i.e. undiffused form, whereby the glare effect otherwise experienced as a result of light rays passing through such bore, adjacent to light rays passing through the portion of the lens body immediately surrounding such bore, is substantially reduced. The plug means are adapted to be removeable received in the bore and when so received therein, provide an opaque or at least semi-opaque barrier to light rays attempting to pass thru such bore.

According to another preferred embodiment, there is provided a plug member adapted to be removably received in the positioning hole in a lens body. The plug member is preferably of a size and shape comparable to the size and shape of the positioning hole and is adapted to be securely retained therein. The plug is preferably opaque, or at least semi-opaque, so that when inserted in the positioning hole, the plug prevents light rays otherwise passing through such positioning hole to continue toward the retina, at least not in a recognizable, or undiffused, condition.

The invention further includes the method of seating within an eye an intraocular lens having a positioning hole, comprising: positioning the lens within the eye with an instrument whose tip is inserted in the positioning hole of the lens, removing the tip of the instrument from the positioning hole after the lens has been seated, inserting into the positioning hole, a plug providing an at least semi-opaque barrier to light rays attempting to pass through the positioning hole and removably retaining said plug in the positioning hole.

BRIEF DESCRIPTION OF THE DRAWINGS

For a better understanding of the present invention, together with other and further objects thereof, reference is made to the following description, taken in connection with the accompanying drawings, and its scope will be pointed out in the appended claims.

Referring now to the drawings.

SPECIFIC DESCRIPTION

Figure 1:
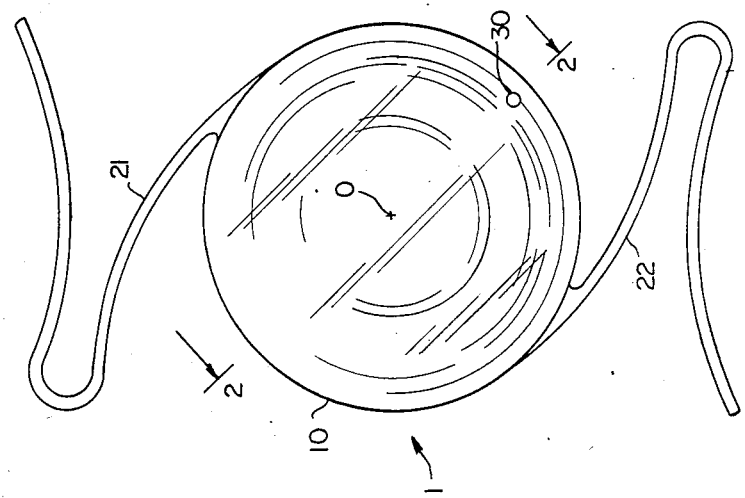
FIG. 1 is a front elevational view of the intraocular lens embodying a preferred form of the present invention.

Referring now to the drawings, reference numeral 1, in FIG. 1, generally indicates an intraocular artificial lens according to a preferred embodiment of the present invention. The lens 1 can be formed of any suitable material compatible with the environment of the human eye, such as a non-toxic plastic, for example, polymethylmethacrylate.

Figure 2:
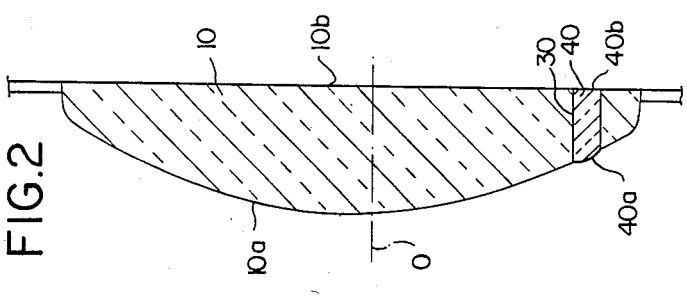
FIG. 2 is a partial, enlarged, transverse sectional view along line 2—2 of FIG. 1.

The lens 1 includes a medial, light-focusing, lens body, or optic, 10 having, for example, as seen in FIG. 2, a convex anterior surface 10a and a generally flat posterior surface 10b, each in a plane generally transverse to the optical axis "O" of the lens body 10. According to the present invention, lens 1 further includes a position-fixation means having a pair of opposed curved position-fixation members 21, 22 which are preferably resilient filaments of PMMA, or similar material, intergrally connected with the lens body.

The lens body 10 is preferably round and the position-fixation members 21, 22 are preferably connected to opposite peripheral regions of such lens body so as to extend in generally diametrically opposite directions.

The lens 1 preferably further includes a bore, or positioning hole, 30 preferably located in a peripheral region of the optic 10 and extending thru the lens body from the anterior surface 10a to the posterior surface 10b thereof, forming a thruopening in the lens body. In use, the lens 1 is inserted through the cornea incision 12 (see FIG. 4) in conventional manner. Inside the eye, the lens is manipulated in conventional manner by use of a conventional surgical instrument having a hooked-pointed tip which may also be inserted through the incision 12. After the tip of the instrument is received in bore 30 of the lens 1, the surgeon moves the instrument to manipulate the lens within the eye for proper seating thereof in the manner indicated in FIG. 4.

Figure 3:
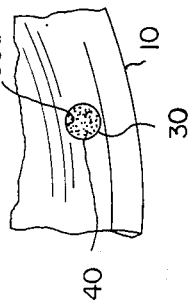
FIG. 3 is an enlarged fragmentary view of the portion of the lens body containing the plug received in the positioning hole as shown in FIGS. 1 and 2.

As seen in FIGS. 1, 2 and 3 bore 30 is preferably in the form of a cylindrical "thrubore" having cylindrical walls 30a extending generally parallel to the optical axis "O". According to a preferred embodiment of the present invention, there is provided a preferably generally cylindrical plug member 40 incorporating masking means in a form to be described below, and having axially opposed transverse end walls 40a, 40b.

Figure 4:
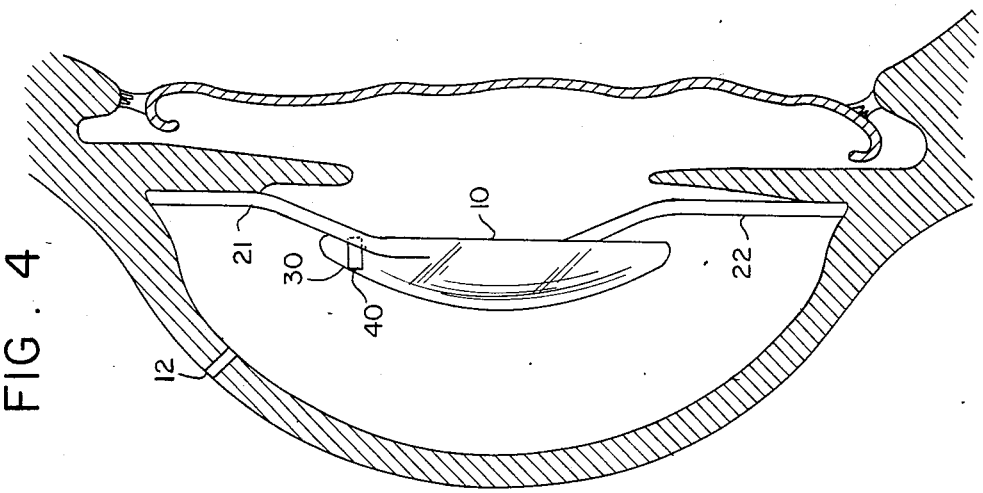
FIG. 4 is a side elevational view of the intraocular lens represented in FIG. 1, showing the latter seated in a eye.

FIG. 4 illustrates the lens according to a preferred embodiment, seated in the anterior chamber of the eye, with bore 30 generally parallel to the optical axis "O" and illustrating that, particularly if the lens 1 were to become decentered, the bore 30 is in the path of the light rays entering through the cornea and being focused by lens body 10 on the retina.

Positioning hole 30 would normally be filled with the fluid in the eye with the above described glare effect as a result. According to the invention, glare elimination or at least, reduction, is achieved by providing plug 40 with masking means and inserting such plug in the bore 30 preferably extending from the anterior surface 10a of the lens body 10 to the posterior surface 10b. The masking means is preferably incorporated in plug 40 by making the latter translucent, i.e. semi-opaque or opaque by any of a number of different processes. For example, an opaque coating may be applied to one or both end faces 40a, 40b or one or both such faces may be etched to a rough finish, or it may be sufficient to leave one or the other of such faces unground or at least not optically smooth. Finally, the plug 40 may be made of a material which is pigmented, or otherwise not transparent.

Figure 5:
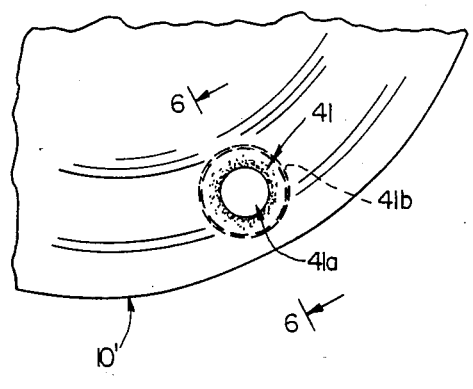
FIG. 5 is an enlarged fragmentary view of a portion of a lens body containing the positioning hole with a plug received therein according to another embodiment of the invention.
Figure 6:
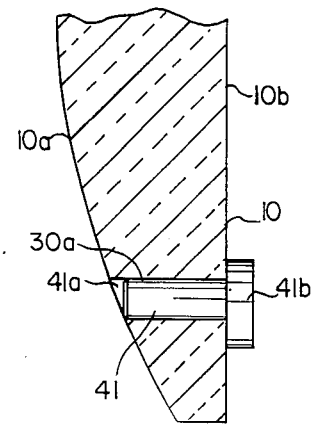
FIG. 6 is a fragmentary transverse sectional view along line 6—6 of FIG. 5.

FIGS. 5 and 6 illustrate another preferred embodiment in which the plug means is a plug 41 having a threaded shank 41a and a head 41b further illustrated in FIG. 9a and described below. Plug 41 is threadedly received in positioning hole 30a which preferably has a female thread adapted to receive the male thread of the shank 41a.

Figure 7:
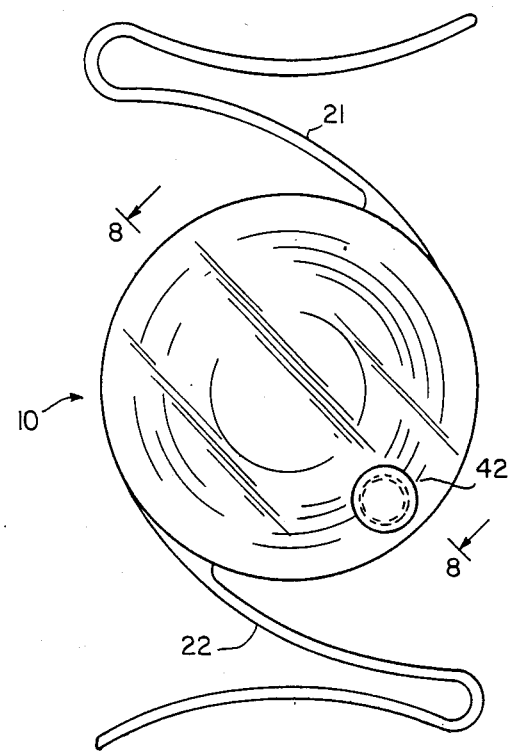
FIG. 7 is a front elevational view of another preferred embodiment of lens according to the present invention.
Figure 8:
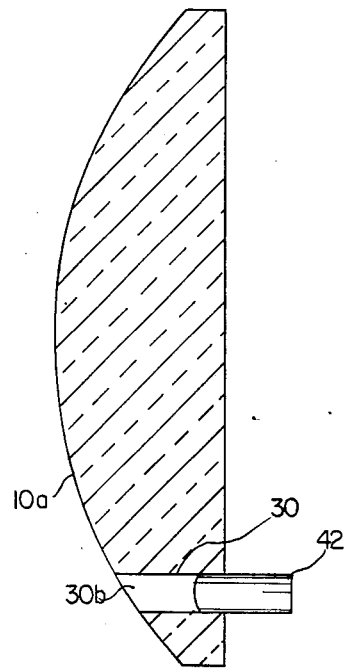
FIG. 8 is a partial, enlarged, transverse, sectional view along Line 8—8 of FIG. 7.

FIGS. 7 and 8 illustrate a still further preferred embodiment of the present invention, namely, one in which an optic 10 cooperates with a plug 42 partially inserted in the bore 30 of the optic. The lens is preferably inserted into the eye in this assembled condition. The portion of the bore 30 which is still open i.e. the anterior portion is used as the positioning hole and after the lens is manipulated into proper seating position, a plier-like surgical tool may be used to press the plug 42 the remainder of the way into the bore 30. Plug 42 is preferably of the type illustrated in FIG. 9c and described below.

The masking means incorporated in the plug 40, 41, 42 prevents light rays from passing therethrough or, at least, from passing therethrough in undiffused form. Thus, light rays refracted in a region exhibiting one index of refraction will not be adjacent to light rays refracted in a region exhibiting another index of refraction, since the positioning hole, instead of being filled with transparent fluid will, in accordance with the present invention be filled with a plug which is at least semi-opaque.

Of course, the masking means need not be located on the surface of the plug, but could instead be located elsewhere in the plug, so long as such masking means is in the path of the light rays in question. If the material of the plug itself comprises the masking means, such material is preferably pigmented with a dark blue color to form an opaque or translucent material, and such opaque or semi-opaque coloring could extend throughout the material of the entire plug.

According to a preferred embodiment of the present invention a plug means such as plug 40 is adapted to be inserted into and releasably retained in positioning hole 30. The plug means 40 preferably, though not necessarily, is comprised of a material which is the same as the material of the optic portion of the lens, for example, PMMA or Prolene. Preferably, the plug means has a cylindrical body adapted to be pressed or screwed into the positioning hole 30 for substantially filling the latter. Thus, according to one embodiment of the present invention, the plug means 40 is in the form of a cylindrical plug 41 which, as seen in FIG. 9c has an outer surface having a diameter only slightly larger than the diameter of the positioning hole 30 in the optic so as to be capable of being press-fitted therein. As is well known, a diameter difference of only one or two ten-thousandths of an inch suffices for this purpose.

Figures 9A, 9B:
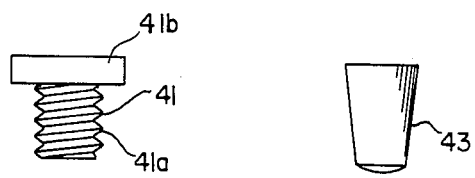
FIG. 9a is a side elevational, enlarged, view of a plug according to one embodiment of the present invention.
FIG. 9b is a side elevational, enlarged, view of another embodiment of a plug according to the present invention.
Figure 9C:
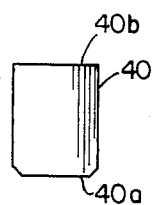
FIG. 9c is a side elevational, enlarged, view of still a further embodiment of a plug according to the present invention.

Alternatively, the plug means may be in the form of a plug 43, which, as seen in FIG. 9b has a substantially cylindrical but slightly conical outer surface. Preferably, in such construction, the smaller diameter of such conical surface is only slightly smaller than the diameter of the positioning hole while the diameter of the conical surface at the larger axial end thereof is only slightly larger than the diameter of the positioning hole. Typically, such positioning holes have a diameter of 0.3 mm or 0.5 mm. The plug means 40, 43 preferably have a pair of axially opposed end faces the shape of whose surfaces preferably corresponds generally to the shape of the respective surface of the optic of surrounding the positioning hole. Thus end face 40 a will, in the illustrated embodiment, have a convexly shaped surface corresponding to the convex shape of the anterior surface of the optic 10 in the region surrounding the positioning hole 30 while the other end face, 40b will be generally flat so as to correspond to the surface of the optic portion surrounding the positioning hole at the posterior side 10b of the optic. The axial length of plug 40, 43 and the length of shank 41a is preferably substantially equal to the length of the axial dimension of the positioning hole 30.

It will be understood that in accordance with a still further embodiment of the present invention the head portion 41b may extend only axially and need not include a radially extending collar in order to be able to be grasped by the appropriate surgical instrument. Those plug embodiments which do not have a head portion can be inserted and/or removed from the positioning hole by a plier-like surgical instrument, capable of supporting one face of the lens with one jaw part while pressing the plug into the positioning hole with the other jaw part. Similarly, removal of a plug such as plug 40, from the positioning hole, should such ever be required for repositioning of the lens within the eye, can be accomplished with a plier-like instrument having a first jaw part with a projection similar in shape to the plug but of smaller diameter and adapted to push against one axial end face of the plug while the other jaw part is adapted to support the corresponding face of the optic while the projecting portion of the other jaw pushes the plug through the positioning hole and into a corresponding hole in such other jaw part of the surgical instrument.

While preferred materials for the plug are PMMA or Prolene, it will be understood that any other materials compatible with the interior of the human eye and of sufficient stiffness to be capable of insertion and removal into and out of a positioning hole in an optic and compatible with the material of such optic, may be used. Preferably the material used is "dark blue PMMA" or "dark blue Prolene" both of which are materials which are tinted a dark blue color throughout. Alternatively an optically transparent material may be used and the end walls of the plug may be coated with an opaque or at least a semi-opaque material. Semi-opaqueness may be obtained by leaving one or both of the end faces of the plug in an unfinished, i.e. in unground condition, so that light rays striking such surface will be diffused and will not be transmitted to the retina in recognizable form.

In use, the lens seen in FIG. 4 will be implemented for seating within the eye by use of the positioning hole 30. Thereafter, the tip of the positioning instrument is removed from the positioning hole and a plug means such as plug 40, 41, 43 is inserted into the eye through the corneo-scleral incision 12 and held in position adjacent one end of the positioning hole and in axial alignment therewith. Thereafter, the plug is pressed, or threaded, into the positioning hole until it is securely, but releasably, retained therein.

Alternatively, the plug means may be partly inserted in a positioning hole prior to insertion of the lens into the eye. The lens, with the partly inserted plug means, is then seated in the eye using, for the positioning instrument, the portion 30b of the positioning hole which remains unobstructed. After the lens has been properly seated in the eye and the surgical instrument used for seating has been withdrawn from the positioning hole, the plug means is forced the remainder of the way into the positioning hole substantially filling the latter. According to this latter method, the difficulty of aligning the plug means with the positioning hole in the eye is avoided.

While there have been described what are at present considered to be the preferred embodiments of this invention, it will be obvious to those skilled in the art that various changes and modification may be made therein without departing from the invention, and it is, therefore, aimed to cover all such changes and modifications as fall within the true spirit and scope of the invention.

What is claimed:

1. In an intraocular lens adapted to be inserted into an eye, a lens body for focusing light on the retina, said lens body comprising:

anterior and posterior optically polished surfaces shaped to focus, on the retina of the eye, light rays entering the eye, a through bore extending from one to the other of said surfaces, said through bore adapted to receive therein the tip of a surgical instrument used to manipulate the lens body within the eye, and plug means adapted to be removably received in said bore after the lens is seated in the eye, said plug means being at least semi-opaque for preventing light rays from passing through the bore toward the retina in a recognizable form when said plug means is received therein, whereby the glare effect otherwise experienced as a result of light rays passing through such bore, adjacent to light rays passing through the portion of the lens body immediately surrounding said bore, is, at least substantially, reduced.

2. In an intraocular lens according to claim 1, wherein said bore is generally cylindrical.

3. In an intraocular lens according to claim 2, wherein said plug means is substantially cylindrical and has a diameter approximately equal to the diameter of said cylindrical bore but sufficiently larger than the diameter of said bore so as to provide an interference fit therebetween when said plug means is inserted into said bore.

4. In an intraocular lens according to claim 2, wherein said plug means is substantially cylindrical and substantially the same size as said bore but has an axial slight taper, the diameter at the small end of said taper being slightly smaller than the diameter of said bore and the diameter at the large end of said taper being slightly larger than the diameter of said bore whereby said plug means can be readily inserted into, and releasably held in, said bore.

5. In an intraocular lens according to claim 2, wherein said plug means is generally cylindrical and has a threaded outer surface and said bore is adapted to threadedly receive said plug means.

6. In an intraocular lens according to claim 2, wherein said plug means is generally cylindrical and has a length approximately equal to the depth of said bore, said plug means having a first axial end face adapted to correspond generally to the shape of the anterior surface of said lens body in the region of said bore, and a posterior face corresponding generally to the shape of the posterior surface of said lens body in the region of said bore.

7. In an intraocular lens according to claim 1, said plug means having opposite axial ends and adapted to be axially received in said positioning hole, said plug means further comprising a head portion intregral with one axial end thereof, said head portion extending axially beyond the corresponding surface of said lens body when said plug means is fully inserted in said positioning hole and said head portion being adapted to be grasped by a surgical instrument for later withdrawal of said plug from said bore should such become desirable.

8. In an intraocular lens according to claim 7, wherein said head portion of said plug means includes a collar portion extending radially outwardly from the remainder of said plug means at said one axial end thereof.

9. A plug for closing the cylindrical positioning hole provided in the optic of an intraocular lens, said plug being of generally cylindrical shape and being adapted to be releasably received in the positioning hole, and said plug comprising masking means for providing an at least semi-opaque barrier to light rays directed generally axially there through.

10. A plug for an intraocular lens according to claim 9, wherein said cylindrical outer surface is slightly axially tapered to form a conical outer surface.

11. A plug for an intraocular lens according to claim 9, wherein the cylindrical outer surface comprises a helical thread.

12. A plug for an intraocular lens according to claim 9, wherein said plug is made of a material chosen from the group consisting of PMMA and Prolene.

13. A plug for an intraocular lens, according to claim 12, said plug having axially opposed end faces, wherein at least one of the end faces of said plug is not optically ground, for diffusing light rays passing there through.

14. A plug for an intraocular lens, according to claim 12, said material being tinted a dark blue color and said tint comprising said masking means.

15. A plug for an intraocular lens according to claim 9, wherein the outer cylindrical surface of said plug is adapted to be press-fitted into said positioning hole.

16. In a method of seating within an eye an intraocular lens having a positioning hole, comprising:

positioning the lens within the eye with an instrument whose tip is inserted in the positioning hole of the lens, removing the tip of the instrument from the positioning hole after the lens has been seated, inserting into the positioning hole, a plug providing an at least semi-opaque barrier to light rays attempting to pass through the positioning hole, and removably retaining said plug in the positioning hole.

17. The method according to claim 16, wherein said step of inserting the plug comprises inserting a cylindrical plug into the eye, holding said cylindrical plug in substantial axial alignment with the bore and adjacent thereto, and pressing the cylindrical plug into said bore until it is fully received and releasably retained therein.

18. According to claim 15, wherein said step of inserting the plug comprises inserting a cylindrical plug into the eye, holding said cylindrical plug in substantial axial alignment with the positioning hole and adjacent thereto, and rotatably threading the cylindrical plug into said positioning hole until it is securely retained therein.

19. A method according to claim 18, partially inserting the plug into one open end portion of the positioning hole prior to insertion of the lens into the eye, leaving a sufficient portion of the opposite open end portion of the positioning hole unobstructed for insertion of the tip of a surgical positioning instrument, positioning the lens within the eye for proper seating thereof, and, after removal of the tip of the positioning instrument, moving the plug the remainder of the way into the positioning hole for substantially filling the latter, and releasably securely retaining the plug in the positioning hole.

* * * * *